US011529510B2

(12) United States Patent
Leven

(10) Patent No.: US 11,529,510 B2
(45) Date of Patent: Dec. 20, 2022

(54) LEAD INTRODUCERS AND SYSTEMS AND METHODS INCLUDING THE LEAD INTRODUCERS

(71) Applicant: Boston Scientific Neuromodulation Corporation, Valencia, CA (US)

(72) Inventor: Jacob B. Leven, Huntington Beach, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 358 days.

(21) Appl. No.: 16/791,781

(22) Filed: Feb. 14, 2020

(65) Prior Publication Data

US 2020/0261714 A1 Aug. 20, 2020

Related U.S. Application Data

(60) Provisional application No. 62/807,351, filed on Feb. 19, 2019.

(51) Int. Cl.
*A61B 17/34* (2006.01)
*A61N 1/05* (2006.01)
*A61N 1/372* (2006.01)

(52) U.S. Cl.
CPC ............ *A61N 1/05* (2013.01); *A61B 17/3468* (2013.01); *A61N 1/372* (2013.01); *A61B 17/3417* (2013.01)

(58) Field of Classification Search
CPC .. A61B 17/3468; A61B 17/3417; A61N 1/372
See application file for complete search history.

(56) References Cited

U.S. PATENT DOCUMENTS

| | | |
|---|---|---|
| 3,330,278 A | 7/1967 | Santomieri |
| 3,359,978 A | 12/1967 | Smith |
| 3,568,660 A | 3/1971 | Crites et al. |
| 3,677,243 A | 7/1972 | Nerz |
| 4,166,469 A | 9/1979 | Littleford |
| 4,355,646 A | 10/1982 | Kallok et al. |
| 4,449,973 A | 5/1984 | Luther |
| RE31,855 E | 3/1985 | Osborne |
| 4,512,351 A | 4/1985 | Pohndorf |
| 4,608,986 A | 9/1986 | Beranek et al. |
| 4,808,157 A | 2/1989 | Coombs |

(Continued)

FOREIGN PATENT DOCUMENTS

| | | |
|---|---|---|
| EP | 2008686 | 12/2008 |
| WO | 89/00436 | 1/1989 |
| WO | 03011361 | 2/2003 |

OTHER PUBLICATIONS

International Search Report and Written Opinion for PCT Application No. PCT/US2020/018378 dated Aug. 20, 2020.

(Continued)

*Primary Examiner* — Eric D. Bertram
(74) *Attorney, Agent, or Firm* — Branch Partners PLLC; Bruce E. Black

(57) ABSTRACT

A lead introducer includes an integrated sheath/needle including a splittable sheath configured to split a into a first portion and a second portion, a needle having a length and a proximal end region, and a hub coupled to the proximal end regions of the splittable sheath and the needle and configured to split into a first portion and a second portion. The needle is permanently attached to either the first portion of the hub or the first portion of the splittable sheath (or both) so that when the hub is split into the first and second portions, the needle remains attached to the first portion of the hub or the first portion of the splittable sheath.

20 Claims, 13 Drawing Sheets

(56) References Cited

U.S. PATENT DOCUMENTS

| | | |
|---|---|---|
| 5,125,904 A | 6/1992 | Lee |
| 5,255,691 A | 10/1993 | Otten |
| 5,312,355 A | 5/1994 | Lee |
| 5,320,602 A | 6/1994 | Karpiel |
| 5,380,290 A | 1/1995 | Makower et al. |
| 5,409,469 A | 4/1995 | Schaerf |
| 5,441,504 A | 8/1995 | Pohndorf et al. |
| 5,713,867 A | 2/1998 | Morris |
| 5,741,233 A | 4/1998 | Riddle et al. |
| 5,752,937 A | 5/1998 | Otten et al. |
| 5,755,693 A | 5/1998 | Walker et al. |
| 5,931,863 A | 8/1999 | Griffin, III et al. |
| 6,080,141 A | 6/2000 | Castro et al. |
| 6,181,969 B1 | 1/2001 | Gord |
| 6,251,119 B1 | 6/2001 | Addis |
| 6,358,460 B1 | 3/2002 | Hunt, Jr. et al. |
| 6,454,744 B1 | 9/2002 | Spohn et al. |
| 6,494,860 B2 | 12/2002 | Rocamora et al. |
| 6,516,227 B1 | 2/2003 | Meadows et al. |
| 6,582,390 B1 | 6/2003 | Sanderson |
| 6,609,029 B1 | 8/2003 | Mann et al. |
| 6,609,032 B1 | 9/2003 | Woods et al. |
| 6,641,564 B1 | 11/2003 | Kraus |
| 6,645,178 B1 | 11/2003 | Junker et al. |
| 6,712,791 B2 | 3/2004 | Lui et al. |
| 6,741,892 B1 | 5/2004 | Meadows et al. |
| 6,749,600 B1 | 6/2004 | Levy |
| 6,758,854 B1 | 7/2004 | Butler et al. |
| 6,869,416 B2 | 3/2005 | Windheuser et al. |
| 6,939,327 B2 | 9/2005 | Hall et al. |
| 7,001,396 B2 | 2/2006 | Glazier et al. |
| 7,014,626 B2 | 3/2006 | Sanderson |
| 7,101,353 B2 | 9/2006 | Lui et al. |
| 7,192,433 B2 | 3/2007 | Osypka et al. |
| 7,244,150 B1 | 7/2007 | Brase |
| 7,359,755 B2 | 4/2008 | Jones et al. |
| 7,437,193 B2 | 10/2008 | Parramon |
| 7,450,997 B1 | 11/2008 | Pianca et al. |
| 7,524,305 B2 | 4/2009 | Moyer |
| 7,672,734 B2 | 3/2010 | Anderson |
| 7,744,571 B2 | 6/2010 | Fisher et al. |
| 7,761,165 B1 | 7/2010 | He |
| 7,783,359 B2 | 8/2010 | Meadows |
| 7,792,590 B1 | 9/2010 | Pianca et al. |
| 7,809,446 B2 | 10/2010 | Meadows |
| 7,887,733 B2 | 2/2011 | Moyer |
| 7,909,798 B2 | 3/2011 | Osypka |
| 7,938,806 B2 | 5/2011 | Fisher et al. |
| 7,941,227 B2 | 5/2011 | Barker |
| 7,949,395 B2 | 5/2011 | Kuzma |
| 7,974,706 B2 | 7/2011 | Moffitt et al. |
| 7,985,232 B2 | 7/2011 | Potter et al. |
| 7,993,305 B2 | 8/2011 | Ye et al. |
| 8,043,263 B2 | 10/2011 | Helgeson et al. |
| 8,105,287 B2 | 1/2012 | Fisher et al. |
| 8,105,315 B2 | 1/2012 | Johnson et al. |
| 8,112,159 B2 | 2/2012 | Harris et al. |
| 8,137,317 B2 | 3/2012 | Osypka |
| 8,147,456 B2 | 4/2012 | Fisher et al. |
| 8,175,710 B2 | 5/2012 | He |
| 8,180,461 B2 | 5/2012 | Mamo et al. |
| 8,224,450 B2 | 7/2012 | Brase |
| 8,271,094 B1 | 9/2012 | Moffitt et al. |
| 8,273,059 B2 | 9/2012 | Nardeo et al. |
| 8,295,944 B2 | 10/2012 | Howard et al. |
| 8,348,899 B2 | 1/2013 | Chesnin et al. |
| 8,364,278 B2 | 1/2013 | Pianca et al. |
| 8,377,006 B2 | 2/2013 | Tal et al. |
| 8,382,715 B2 | 2/2013 | Nardeo et al. |
| 8,391,985 B2 | 3/2013 | McDonald |
| 8,583,237 B2 | 11/2013 | Bedenbaugh |
| 8,688,235 B1 | 4/2014 | Pianca et al. |
| 8,831,742 B2 | 9/2014 | Pianca et al. |
| 8,849,422 B2 | 9/2014 | Pianca |
| 9,510,857 B2 | 12/2016 | Barker |
| 9,931,109 B2 | 4/2018 | Burckhardt et al. |
| 9,987,435 B2 | 6/2018 | Colantonio |
| 2002/0111617 A1 | 8/2002 | Cosman et al. |
| 2005/0021119 A1 | 1/2005 | Sage et al. |
| 2005/0055027 A1 | 3/2005 | Yeung et al. |
| 2005/0107861 A1 | 5/2005 | Harris et al. |
| 2005/0113860 A1 | 5/2005 | Keidar |
| 2007/0150036 A1 | 6/2007 | Anderson |
| 2008/0300538 A1 | 12/2008 | Schweikert et al. |
| 2009/0187222 A1 | 7/2009 | Barker |
| 2009/0248111 A1 | 10/2009 | Pianca et al. |
| 2009/0254019 A1 | 10/2009 | Gehl et al. |
| 2009/0259283 A1 | 10/2009 | Brandt et al. |
| 2009/0276021 A1 | 11/2009 | Meadows et al. |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0054402 A1 | 3/2011 | Tanabe et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0218549 A1 | 9/2011 | Barker |
| 2011/0224680 A1 | 9/2011 | Barker |
| 2011/0224681 A1 | 9/2011 | McDonald |
| 2011/0230893 A1 | 9/2011 | Barker |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0202928 A1 | 8/2012 | Barker et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2012/0323254 A1 | 12/2012 | Bonde et al. |
| 2013/0053851 A1 | 2/2013 | Schmitz et al. |
| 2013/0105071 A1 | 5/2013 | DiGiore et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039586 A1 | 2/2014 | Barker et al. |
| 2014/0039587 A1 | 2/2014 | Romero |
| 2014/0073926 A1 | 3/2014 | Rajendran et al. |
| 2014/0276927 A1 | 9/2014 | Barker |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0073431 A1 | 3/2015 | Barker |
| 2015/0073432 A1* | 3/2015 | Barker .............. A61N 1/056 606/129 |
| 2015/0151113 A1 | 6/2015 | Govea et al. |
| 2016/0317800 A1* | 11/2016 | Barker .............. A61B 17/3468 |
| 2017/0340891 A1 | 11/2017 | Boggs et al. |

OTHER PUBLICATIONS

Invitation to Pay Additional Fees for PCT Application No. PCT/US2020/018378 mailed Jun. 24, 2020.

* cited by examiner

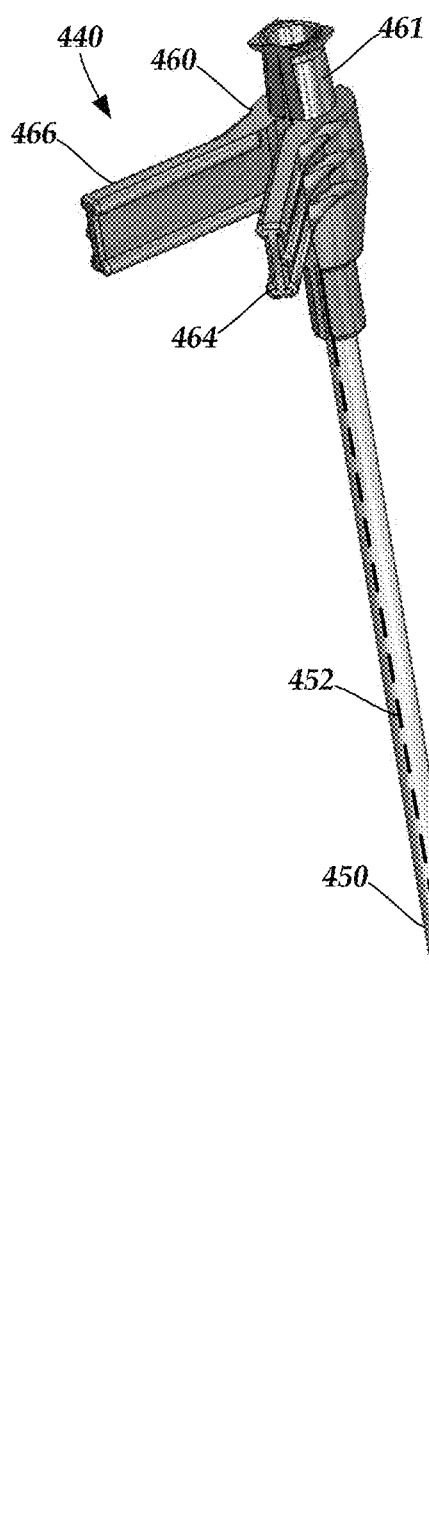
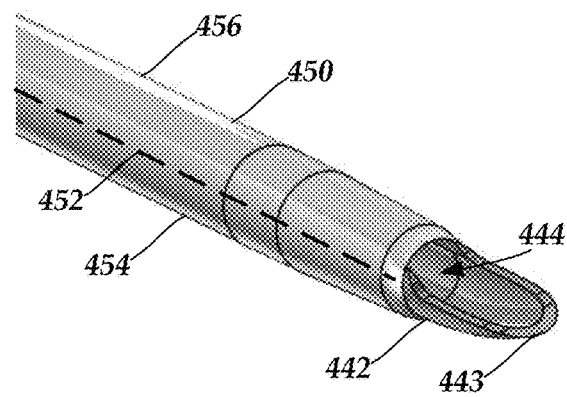
Fig. 4B
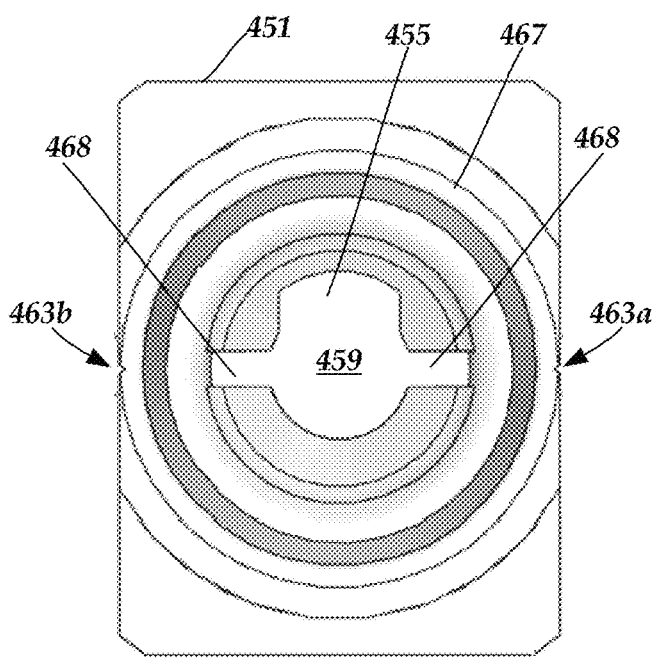
Fig. 4G
Fig. 4A

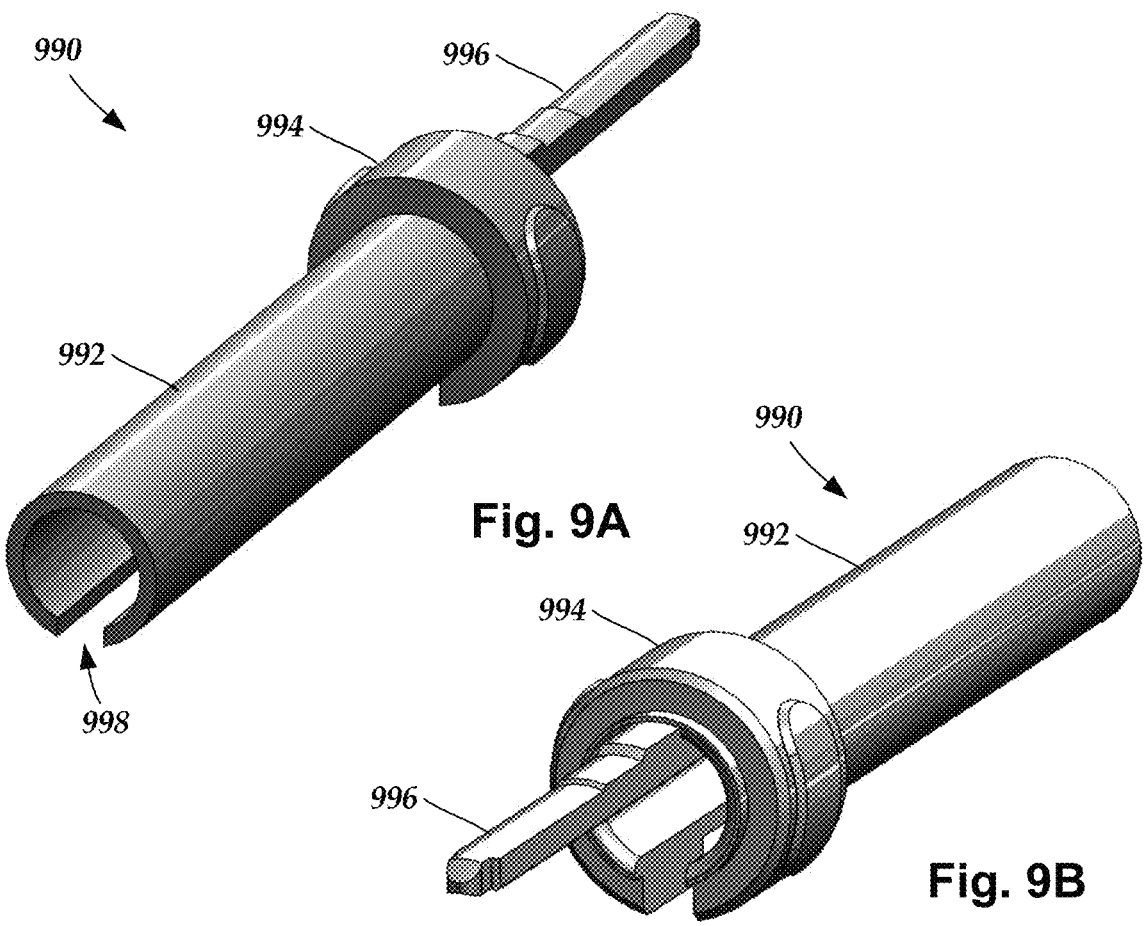
Fig. 9A
Fig. 9B
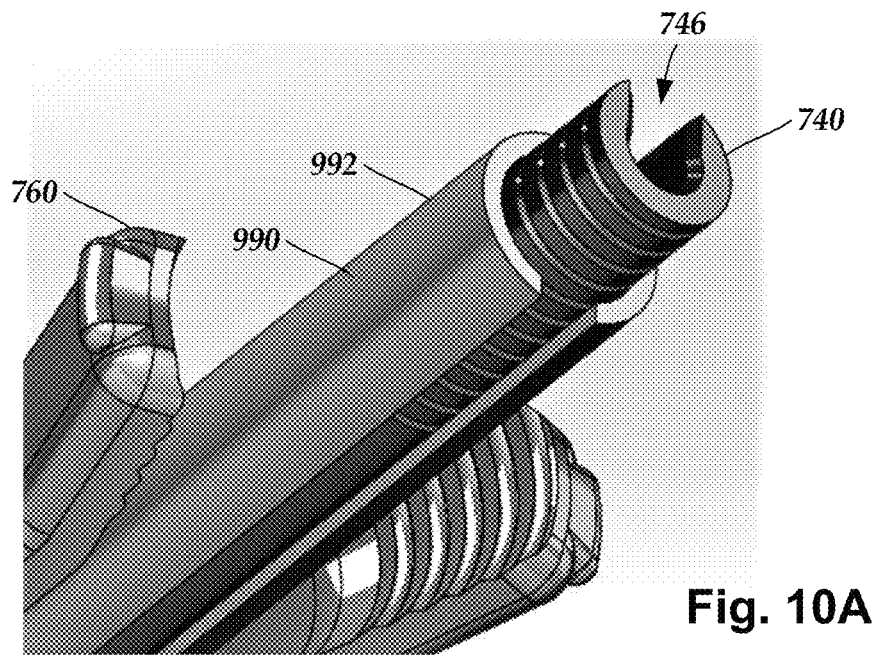
Fig. 10A

LEAD INTRODUCERS AND SYSTEMS AND METHODS INCLUDING THE LEAD INTRODUCERS

CROSS-REFERENCE TO RELATED APPLICATIONS

This application claims the benefit under 35 U.S.C. § 119(e) of U.S. Provisional Patent Application Ser. No. 62/807,351, filed Feb. 19, 2019, which is incorporated herein by reference.

FIELD

The present invention is directed to the area of implantable stimulation systems and methods of making and using the systems. The present invention is also directed to a lead introducer for facilitating insertion of implantable stimulation leads into patients, as well as methods of making and using the lead introducers and stimulation leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a lead introducer that includes an integrated sheath/needle including a splittable sheath having a length and a proximal end region and configured to split along the length of the splittable sheath into a first portion and a second portion, the splittable sheath defining a sheath lumen, a needle having a length and a proximal end region, the needle defining an open channel extending along the length of the needle, wherein the needle extends through the sheath lumen of the splittable sheath, and a hub coupled to the proximal end regions of the splittable sheath and the needle and configured to split into a first portion and a second portion, the hub defining a port and a hub lumen extending from the port and in communication with the open channel, wherein the needle is permanently attached to the first portion of the hub so that when the hub is split into the first and second portions, the needle remains attached to the first portion of the hub.

In at least some aspects, the hub includes a body and at least two tabs extending from the body, wherein the hub is configured to split, along with the splittable sheath, using the at least two tabs. In at least some aspects, the hub includes a small-bore connector coupled to the body and forming a portion of the port and hub lumen. In at least some aspects, the needle defines a slot along the length of the needle and configured for lateral release of a lead from the open channel of the needle.

In at least some aspects, the lead introducer further includes a needle stylet configured for insertion into the open channel of the needle. In at least some aspects, the needle stylet includes a stylet body and a handle coupled to the stylet body. In at least some aspects, the needle of the integrated sheath/needle includes a body having a length, wherein the body defines two opposing ends that are separated from each other along the length of the body to define a slot. In at least some aspects, the stylet body includes a cylindrical portion and a stiffening portion extending along at least a portion of the cylindrical portion, wherein the stiffening portion is configured to fit in the slot of the needle of the integrated sheath/needle.

In at least some aspects, the needle is permanently attached to the first portion of the splittable sheath so that when the splittable sheath is split into the first and second portions, the needle remains attached to the first portion of the splittable sheath. In at least some aspects, the first portion of the splittable sheath is permanently attached to the first portion of the hub so that when the hub is split into the first and second portions, the first portion of the splittable sheath remains attached to the first portion of the hub. In at least some aspects, the second portion of the splittable sheath is permanently attached to the second portion of the hub so that when the hub is split into the first and second portions, the second portion of the splittable sheath remains attached to the second portion of the hub.

Another aspect is a lead introducer that includes an integrated sheath/needle including a splittable sheath having a length and a proximal end region and configured to split along the length of the splittable sheath into a first portion and a second portion, the splittable sheath defining a sheath lumen, and a needle having a length and a proximal end region and permanently attached to the first portion of the splittable sheath so that when the splittable sheath is split into the first and second portions, the needle remains attached to the first portion of the splittable sheath, the needle defining an open channel extending along the length of the needle.

In at least some aspects, the lead introducer further includes a hub coupled to the proximal end regions of the splittable sheath and the needle, the hub defining a port and a hub lumen extending from the port and in communication with the open channel of the needle, the hub including a body and at least two tabs extending from the body, wherein the hub is configured to split, along with the splittable sheath, using the at least two tabs. In at least some aspects, the needle of the integrated sheath/needle defines a slot configured for lateral release of a lead from the open channel of the needle.

In at least some aspects, the lead introducer further includes a needle stylet configured for insertion into the open channel of the needle. In at least some aspects, the needle of the integrated sheath/needle includes a body having a length, wherein the body defines two opposing ends that are separated from each other along the length of the body to define a slot. In at least some aspects, the needle stylet includes a stylet body and a handle coupled to the stylet body, wherein the stylet body includes a cylindrical portion and a stiffening portion extending along at least a portion of the cylindrical portion, wherein the stiffening portion is configured to fit in the slot of the needle of the integrated sheath/needle.

Yet another aspect is a lead introducer that includes a splittable sheath including a sheath body and a sheath hub coupled to the sheath body, the sheath body having a length and a proximal end region and configured to split along the length of the sheath body into a first portion and a second portion, the splittable sheath defining a sheath lumen; an outer needle including a body and a needle hub coupled to the body, wherein the outer needle is configured for insertion into the sheath lumen, the body and needle hub defining an open channel and a slot extending along a length of the outer needle and configured for lateral release of a lead disposed in the open channel through the slot; and a lead guide configured for insertion over at least a portion of the needle hub to cover a portion of the slot to facilitate insertion of the lead into the open channel of the outer needle.

A further aspect is an insertion kit that includes any of the lead introducers described above; and a stimulation lead configured for implantation into a patient. The stimulation lead includes a lead body having a distal end portion and a proximal end portion, electrodes disposed at the distal end portion of the lead body, terminals disposed at the proximal end portion of the lead body, and conductive wires coupling the electrodes electrically to the terminals; wherein the stimulation lead is insertable through the port of the hub of the lead introducer and into the hub lumen of the hub and the open channel of the needle.

Another aspect is an electrical stimulation system that includes the insertion kit described above, a control module configured to electrically couple to the stimulation lead of the insertion kit, and a connector for connecting the stimulation lead to the control module. The control module includes a housing, and an electronic subassembly disposed in the housing. The connector includes a connector housing defining a port for receiving the proximal end portion of the lead body, and connector contacts disposed in the connector housing, the connector contacts configured to couple to the terminals of the stimulation lead when the proximal end portion of the stimulation lead is received by the connector housing.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic perspective view of one embodiment of the integrated needle/sheath of FIG. 3;

FIG. 4B is a schematic perspective close-up view of one embodiment of a distal end portion of the integrated needle/sheath of FIG. 4A;

FIG. 4G is a partial schematic view into the proximal end of the integrated needle/sheath of FIG. 4A;

FIG. 9A is a schematic perspective view of one embodiment of a lead guide;

FIG. 9B is another schematic perspective view of the lead guide of FIG. 9A from an opposite end;

FIG. 10A is a schematic perspective view of the lead guide of FIG. 9A disposed on the proximal end portion of the outer needle of FIG. 8 and disposed partially within a hub of the splittable member of FIG. 7;

DETAILED DESCRIPTION

The present invention is directed to the area of implantable stimulation systems and methods of making and using the systems. The present invention is also directed to a lead introducer for facilitating insertion of implantable stimulation leads into patients, as well as methods of making and using the lead introducers and stimulation leads.

Suitable implantable electrical stimulation systems include, but are not limited to, a least one lead with one or more electrodes disposed along a distal end of the lead and one or more terminals disposed along the one or more proximal ends of the lead. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 6,175,710; 6,224,450; 6,271,094; 6,295,944; 6,364,278; and 6,391,985; U.S. Patent Application Publications Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Figure 1:
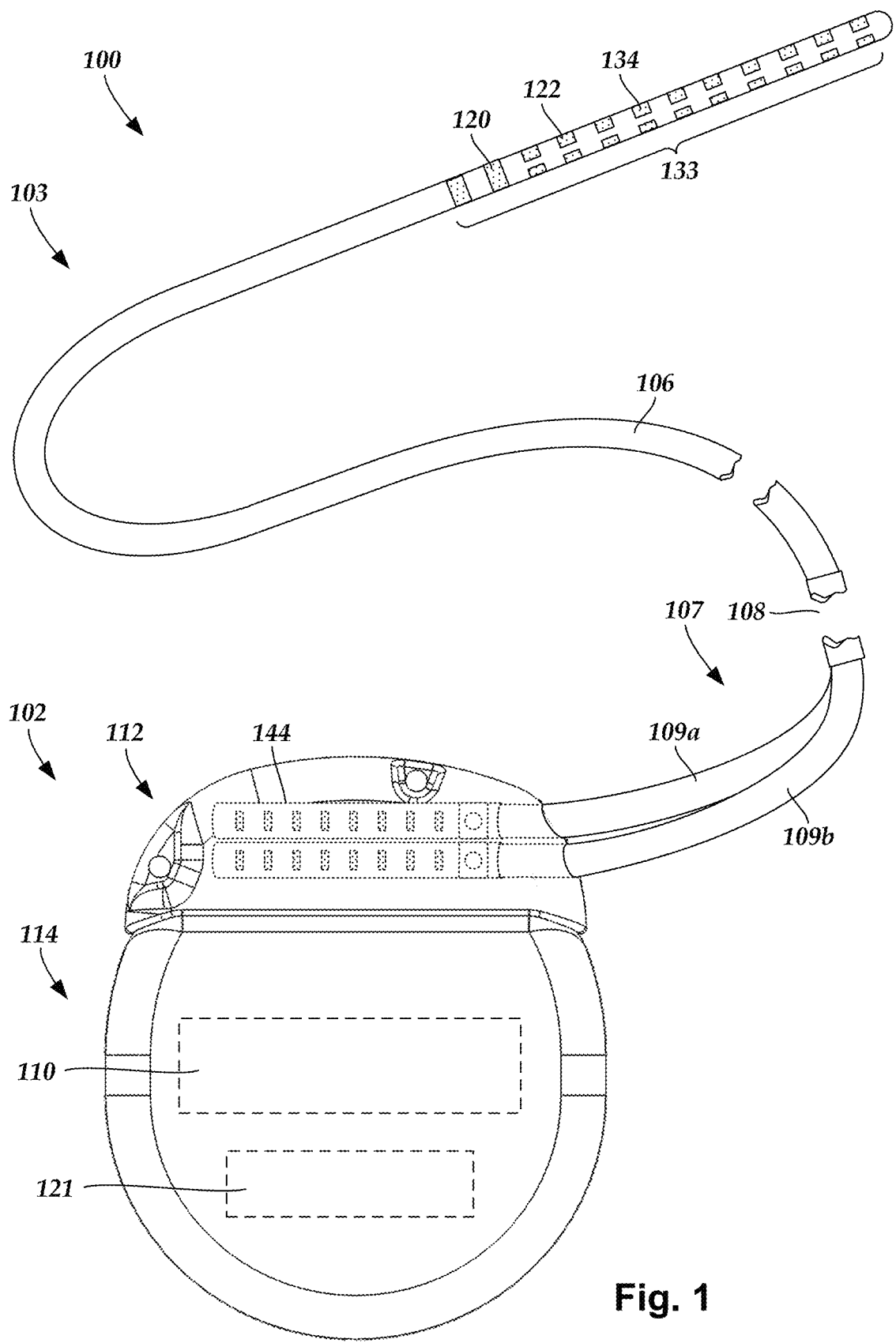
FIG. 1 is a schematic view of another embodiment of an electrical stimulation system that includes a percutaneous lead body coupled to a control module.

FIG. 1 illustrates schematically one embodiment of an electrical stimulation system 100. The electrical stimulation system includes a control module (e.g., a stimulator or pulse generator) 102 and at least one lead 103 coupleable to the control module 102. The lead 103 includes one or more lead bodies 106, an array of electrodes 133, such as electrode 134, and an array of terminals (e.g., 210 in FIGS. 2A and 2B) disposed along the one or more lead bodies 106. In at least some embodiments, the lead is isodiametric along a longitudinal length of the lead body 106. FIG. 1 illustrates one lead 103 coupled to a control module 102. Other embodiments may include two, three, four, or more leads 103 coupled to the control module 102.

The lead 103 can be coupled to the control module 102 in any suitable manner. In at least some embodiments, the lead 103 couples directly to the control module 102. In at least some other embodiments, the lead 103 couples to the control module 102 via one or more intermediate devices. For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 121 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
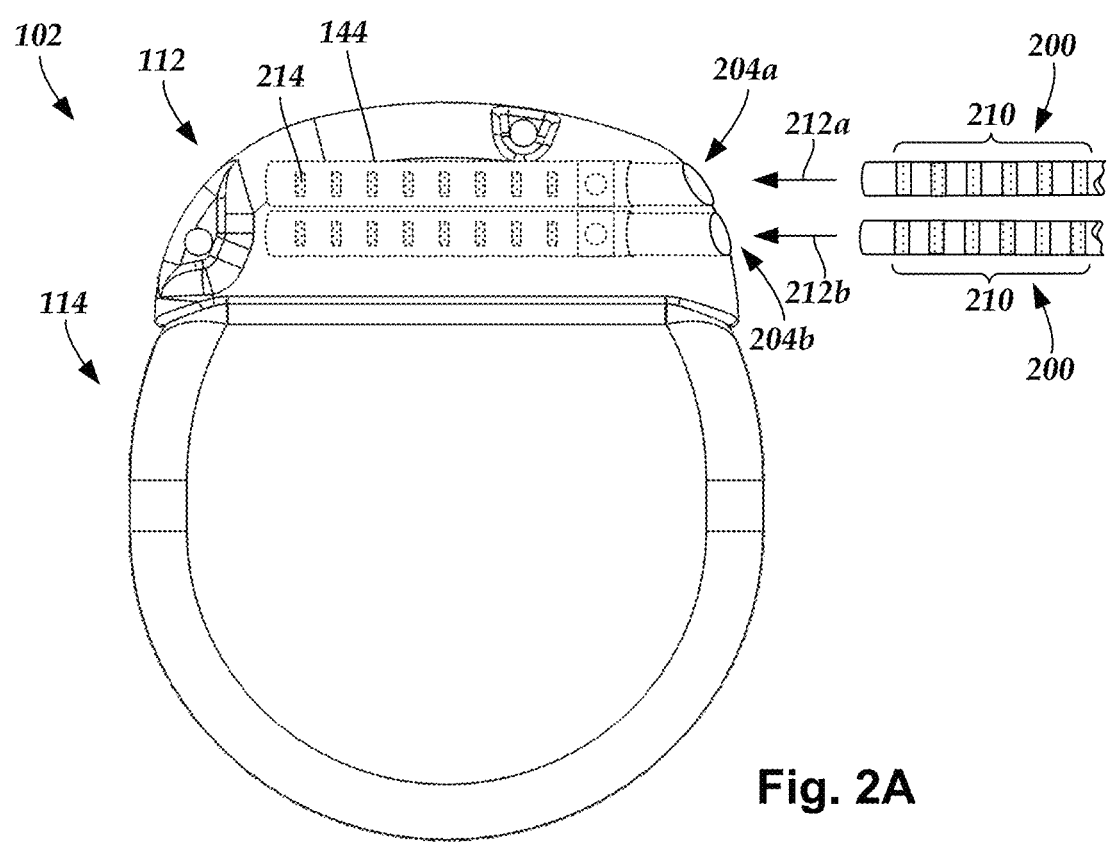
FIG. 2A is a schematic view of one embodiment of a plurality of connector assemblies disposed in the control module of FIG. 1, the connector assemblies configured to receive the proximal portions of the lead bodies of FIG. 1.
Figure 2B:
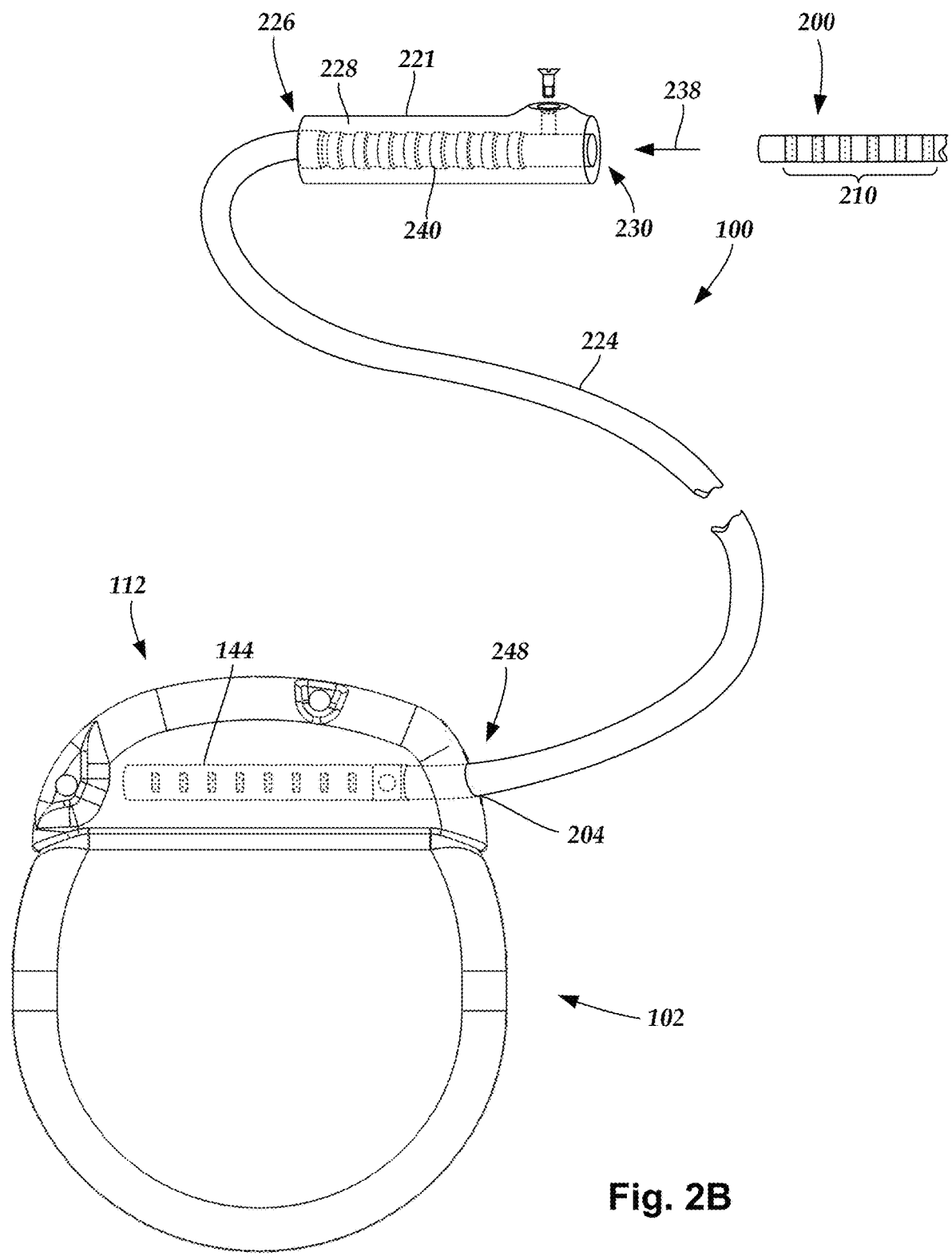
FIG. 2B is a schematic view of one embodiment of a proximal portion of the lead body of FIG. 1, a lead extension, and the control module of FIG. 1, the lead extension configured to couple the lead body to the control module.

Terminals (e.g., 210 in FIGS. 2A and 2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIG. 2A and 240 in FIG. 2B). The connector contacts are disposed in connectors (e.g., 144 in FIGS. 1-2B; and 221 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof. FIG. 2A illustrates two elongated devices 200 coupled to the control module 102. These two elongated devices 200 can be two tails as illustrated in FIG. 1 or two different leads or any other combination of elongated devices.

The control module connector 144 defines at least one port into which a proximal end of the elongated device 200 can be inserted, as shown by directional arrows 212*a* and 212*b*. In FIG. 2A (and in other figures), the connector housing 112 is shown having two ports 204*a* and 204*b*. The connector housing 112 can define any suitable number of ports including, for example, one, two, three, four, five, six, seven, eight, or more ports.

The control module connector 144 also includes a plurality of connector contacts, such as connector contact 214, disposed within each port 204*a* and 204*b*. When the elongated device 200 is inserted into the ports 204*a* and 204*b*, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference in their entireties.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 221 is disposed on the lead extension 224. In FIG. 2B, the lead extension connector 221 is shown disposed at a distal end 226 of the lead extension 224. The lead extension connector 221 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Returning to FIG. 1, at least some of the stimulation electrodes take the form of segmented electrodes that extend only partially around the perimeter (for example, the circumference) of the lead. These segmented electrodes can be provided in sets of electrodes, with each set having electrodes circumferentially distributed about the lead at a particular longitudinal position.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

In FIG. 1, the electrodes 134 are shown as including both ring electrodes 120 and segmented electrodes 122. In some embodiments, the electrodes 134 are all segmented. The segmented electrodes 122 of FIG. 1 are in sets of three (one of which is not visible in FIG. 1), where the three segmented electrodes of a particular set are electrically isolated from one another and are circumferentially offset along the lead 1-3. Any suitable number of segmented electrodes can be formed into a set including, for example, two, three, four, or more segmented electrodes. The lead 103 of FIG. 1 has thirty segmented electrodes 122 (ten sets of three electrodes each) and two ring electrodes 120 for a total of 32 electrodes 134.

Segmented electrodes can be used to direct stimulus current to one side, or even a portion of one side, of the lead. When segmented electrodes are used in conjunction with an implantable pulse generator that delivers current stimulus, current steering can be achieved to more precisely deliver the stimulus to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a perimeter of the lead. This provides precise three-dimensional targeting and delivery of the current stimulus to neural target tissue, while potentially avoiding stimulation of other tissue.

Examples of leads with segmented electrodes include U.S. Patent Application Publications Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/0197375; 2012/0203316; 2012/0203320; 2012/0203321; 2013/0197602; 2013/0261684; 2013/0325091; 2013/0317587;

2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. A lead may also include a tip electrode and examples of leads with tip electrodes include at least some of the previously cited references, as well as U.S. Patent Application Publications Nos. 2014/0296953 and 2014/0343647, all of which are incorporated herein by reference in their entireties. A lead with segmented electrodes may be a directional lead that can provide stimulation in a particular direction using the segmented electrodes.

Conventional percutaneous implantation techniques often include inserting a lead introducer, such as an epidural needle, into a patient. A lead is then inserted into the lead introducer and the lead introducer is positioned at a target stimulation location. When correctly positioned, the lead introducer is removed from the patient, leaving the lead in place. Often the lead introducer is removed from the patient by sliding the lead introducer off the proximal end of the lead. This action, however, may result in movement of the lead so that it is no longer positioned at the desired stimulation location.

Other percutaneous implantation techniques utilize a lateral release lead introducer that includes a multi-piece insertion needle that enables a lead to be laterally separated from the multi-piece insertion needle instead of sliding the needle off the end of the lead. Examples of lateral release lead introducers are found in, for example, U.S. Patent Application Publication Nos. 2011/0224680, 2014/0039586, 2014/0276927, 2015/0073431, 2015/0073432, and 2016/0317800, all of which are incorporated herein by reference in their entireties. These lateral release lead introducers include an outer needle, an inner needle, a splittable member, and a stylet. The four components of these lateral release lead introducers introduce more complexity than the conventional lead introducer discussed above which only uses one or two components (e.g., an epidural needle and an optional stylet). Lateral release lead introducers can be particularly useful for implanting leads have multiple tails, such as the lead 103 illustrated in FIG. 3, or other non-isodiametric arrangements along the lead.

Figure 3:
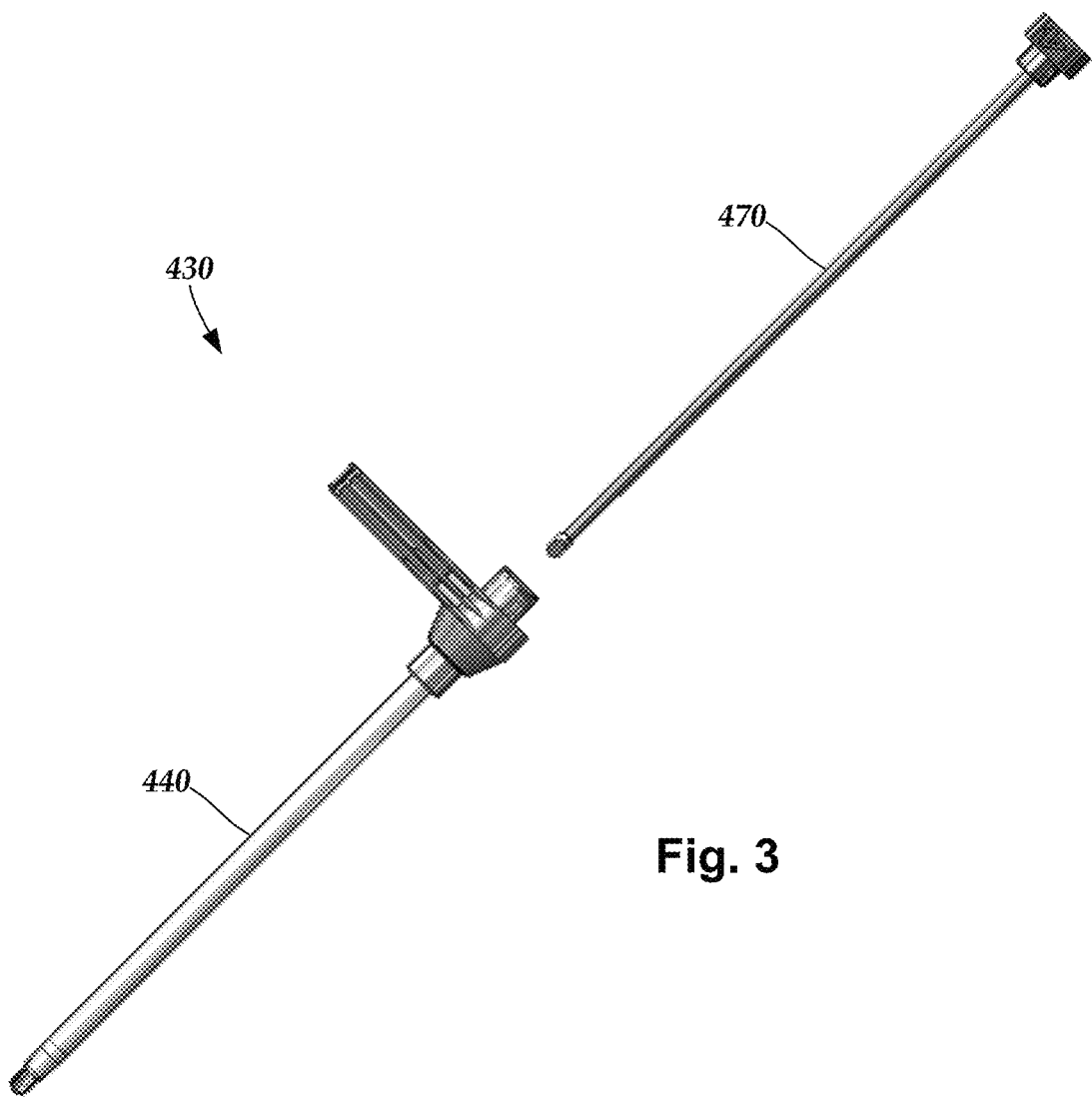
FIG. 3 is a schematic perspective exploded view of one embodiment of a two component lead introducer configured for facilitating implantation of a lead of an electrical stimulation system into a patient, the lead introducer including an integrated needle/sheath and a needle stylet.

To reduce the number of components and complexity, FIG. 3 illustrates a two component lateral release lead introducer 430 having an integrated needle/sheath 440 and a needle stylet 470. The needle stylet 470 is inserted into the integrated needle/sheath 440 and the combination is inserted into the patient. After insertion and location of the lead introducer 430 at or near the implant site, the needle stylet 470 is removed from the integrated needle/sheath 440 and a lead 103 is inserted into the integrated needle/sheath 440 for delivery and placement of the lead at the implant site.

FIGS. 4A to 4F illustrate an integrated needle/sheath 440 which includes a needle 442, a splittable sheath 450, and a hub 460. The needle 442 of the integrated needle/sheath 440 includes a proximal end portion 441 (FIG. 4F), a distal end portion 443 (FIG. 4C), and an open channel 444 (FIG. 4C) that extends along the longitudinal length of the needle. The needle stylet 470 and the lead 103 are sequentially received in the open channel 444 during the implantation procedure.

Figure 4C:
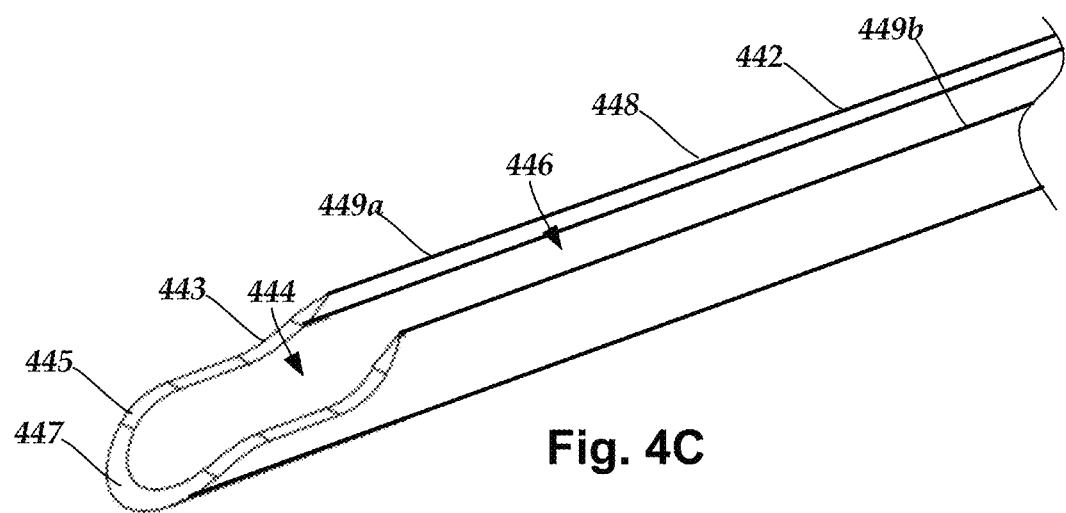
FIG. 4C is a schematic perspective close-up view of one embodiment of a distal end portion of the needle of the integrated needle/sheath of FIG. 4A.

As illustrated in FIG. 4C, the needle 442 further includes a slot 446 along the length of the needle. In some embodiments, the needle 442 has a body 448 that defines two opposing ends 449a, 449b that are separated from each other along the length of the body to define the slot 446. This slot 446 allows for lateral separation of the lead 103 from the needle 442 by laterally passing the lead, initially residing in the open channel 444, through the slot. In at least some embodiments, to facilitate lateral separation, the slot 446 is at least as wide as the diameter of the lead 103. In other embodiments, the lead 103 has a diameter that is larger than the slot 446 of the needle 442. The body of the lead 103 may be formed from a deformable material and the lead is removable from the open channel 444 by applying a lateral force to at least one of the lead 103 or the needle 442 to deform the lead enough to enable the lead to be passed laterally out through the slot 446 in the needle 442.

The needle 442 can be made from any suitable material including, but not limited to, stainless steel or other metal. The distal end portion 443 of the needle 442 may have a slanted face 445 with a sharpened end 447 suitable for piercing patient tissue during insertion of the lead introducer 430 into the patient. At least the sharpened end 447 of the needle 442, and preferably the slanted face, extends distally beyond the distal end of the splittable sheath 450, as illustrated in FIG. 4B. In other embodiments, the distal end portion 443 of the needle 442 may have a Tuohy tip or blunt epidural tip. An optional bend can be provided along the distal end portion of the needle 442 such as, for example, the bend disclosed in U.S. Patent Application Publication No. 2016/0317800, incorporated herein by reference in its entirety.

Returning to FIGS. 4A and 4B, the splittable sheath 450 is arranged to split along the longitudinal length of the splittable sheath 450 into two portions. In at least some embodiments, the splittable sheath 450 includes one or more perforated (or scored, weakened, thinned, or the like) regions 452 extending along at least a portion of the longitudinal length of the splittable sheath 450, as illustrated in FIGS. 4A and 4B. In at least some embodiments, the splittable sheath 450 can be pre-split, perforated, scored, weakened, or thinned only within, or adjacent to, the hub 460 and have no further perforations or the like along the length of the splittable sheath. The splittable sheath can be made of any suitable material including, but not limited to, polymer materials such as high density polyethylene (HDPE), polytetrafluoroethylene (PTFE), or the like. As an example, materials such as PTFE, when extruded, can split easily and reliably in the direction of the extrusion without having to pre-score or perforate.

In at least some embodiments, the splittable sheath 450 is arranged to split along the longitudinal axis into a first portion 454 and a second portion 456. In at least some embodiments, the integrated needle/sheath 440 the needle 442 remains attached to the first portion 454 of the splittable sheath 450 when it is split. The second portion 456 of the splittable sheath 450 separates from the needle 442 and also exposes the slot 446 in the needle to allow the lead 103 to be removed from the open channel 444 in the needle.

Figure 4D:
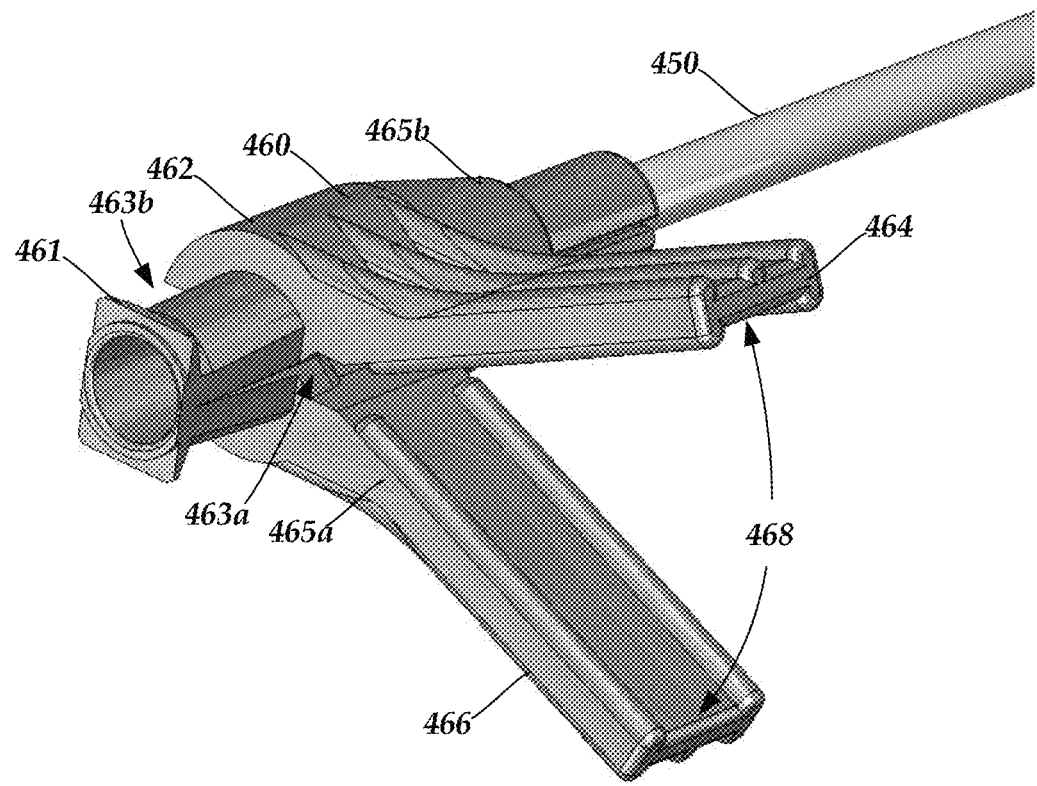
FIG. 4D is a schematic perspective close-up view of one embodiment of a proximal end portion of the integrated needle/sheath of FIG. 4A including the hub.

As illustrated in FIG. 4D, the hub 460 includes a body 462 and at least two pull-apart tabs 464, 466 that extend away from the body 462 of the hub 460. The two pull-apart tabs 464, 466 can be used to separate the splittable sheath 450 (and, at least in some embodiments, the hub 460) into two portions by pulling the two pull-apart tabs away from each other. In some embodiments, the separation process may also include first squeezing the two pull-apart tabs 464, 466 together to initiate separation of one or both of the hub 460 and splittable sheath 450 and then pulling the two pull-apart tabs 464, 466 away from each other to complete the separation.

In at least some embodiments, an angle 468 between the two pull-apart tabs 464, 466 is less than 180, 120, 90, or 60 degrees. In other embodiments, the pull-apart tabs can be 180 degrees apart, as disclosed in U.S. Patent Application Publication Nos. 2011/0224680, 2014/0039586, 2014/0276927, 2015/0073431, and 2015/0073432, all of which are incorporated herein by reference in their entireties. In yet other embodiments, the pull-apart tabs may extend proximally parallel (or at an acute angle no more than 89, 80, 75, 60, or 45 degrees) to the longitudinal axis of the splittable sheath 450 as disclosed in U.S. Patent Application Publication No. 2016/0317800, incorporated herein by reference in its entirety.

In at least some embodiments, the body 462 of the hub 460 includes, at the proximal end of the body, a small-bore connector 461, such as a Luer fitting, which may be used for coupling with other devices. In at least some embodiments, the body 462 (and the small-bore connector 461, if included) can include one or two slits or weakened regions 463a, 463b between the pull-apart tabs 464, 466 to facilitate separation of the body (and small-bore connector, if included) into two portions when the splittable sheath 462 is split and separated into two regions using the two pull-apart tabs 464, 466, as described above.

In at least some embodiments, the small-bore connector 461, such as a Luer fitting, can facilitate a loss of resistance (LOR) procedure. Because entry into the epidural space is a delicate procedure requiring greater precision than may be obtained via fluoroscopy, LOR is used to insert the tip of the needle 442 just barely into the epidural space. The clinician initially inserts the fully-assembled lead introducer 430 into the patient until the tip is near the epidural space. Then, the needle stylet 470 is removed and a syringe filled with air or saline is connected to the needle 442 through the small-bore connector 461. The clinician slowly advances the needle 442 while applying pressure to the syringe plunger. Before the tip of the needle 442 breaches into the epidural space, the tissue occludes the needle tip, preventing fluid from escaping, and providing resistance to the syringe plunger. Once the tip of the needle 442 breaches the epidural space, the fluid can escape the needle tip and the syringe plunger is easily depressed indicating to the clinician that the needle tip has entered the epidural space.

The hub 460 is separable into two parts 465a, 465b using the at least two pull-apart tabs 464, 466. Separating the hub 460 can also lead to separation of the splittable sheath 450 into the two portions 454, 456. In at least some embodiments, the first portion 465a of the hub 460 is attached to the needle 442 using any suitable method or material. For example, the first portion 465a of the hub 460 can be attached to the needle 442 by adhesive or by overmolding of the first portion 465a of the hub 460 onto the needle 442 or by any other suitable attachment method. The first portion 465a of the hub 460 is also attached to the first portion 454 of the splittable sheath 450 so that, when separation of the two portions 465a, 465b of the hub 460 occurs, the first portions 465a of the hub 460, first portion 454 of the splittable sheath 450, and needle 442 remain fixed together. In addition, when separation of the two portions 465a, 465b of the hub 460 occurs, the second portion 465b of the hub 460 and the second portion 456 of the splittable sheath 450 remain fixed together.

In at least some embodiments, the first portion 454 of the splittable sheath 450 may also be attached to the needle 442 by adhesive or by heat shrinking or melting the first portion 454 of the splittable sheath 450 onto the needle 442 or any other suitable method. Preferably, the attachment of the first portion 454 of the splittable sheath 450 to the needle 442 is sufficient so that the splittable sheath 450 remains attached to the needle 442 during insertion of the lead introducer 430 into the patient. In at least some embodiments, the attachment of the first portion 454 of the splittable sheath 450 to the needle 442 may allow some disengagement of the first portion 454 from the needle 442 after splitting of the hub 460 and splittable sheath 450.

Figure 4E:
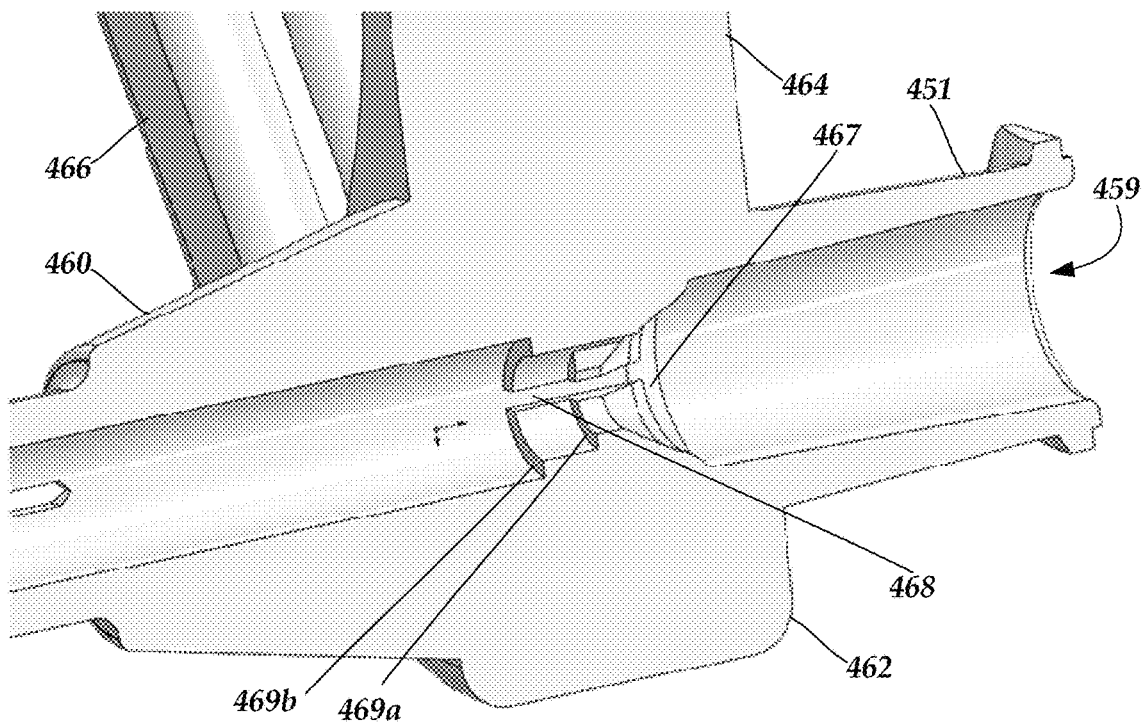
FIG. 4E is a schematic cut-away view of one embodiment of the hub of the integrated needle/sheath of FIG. 4D.
Figure 4F:
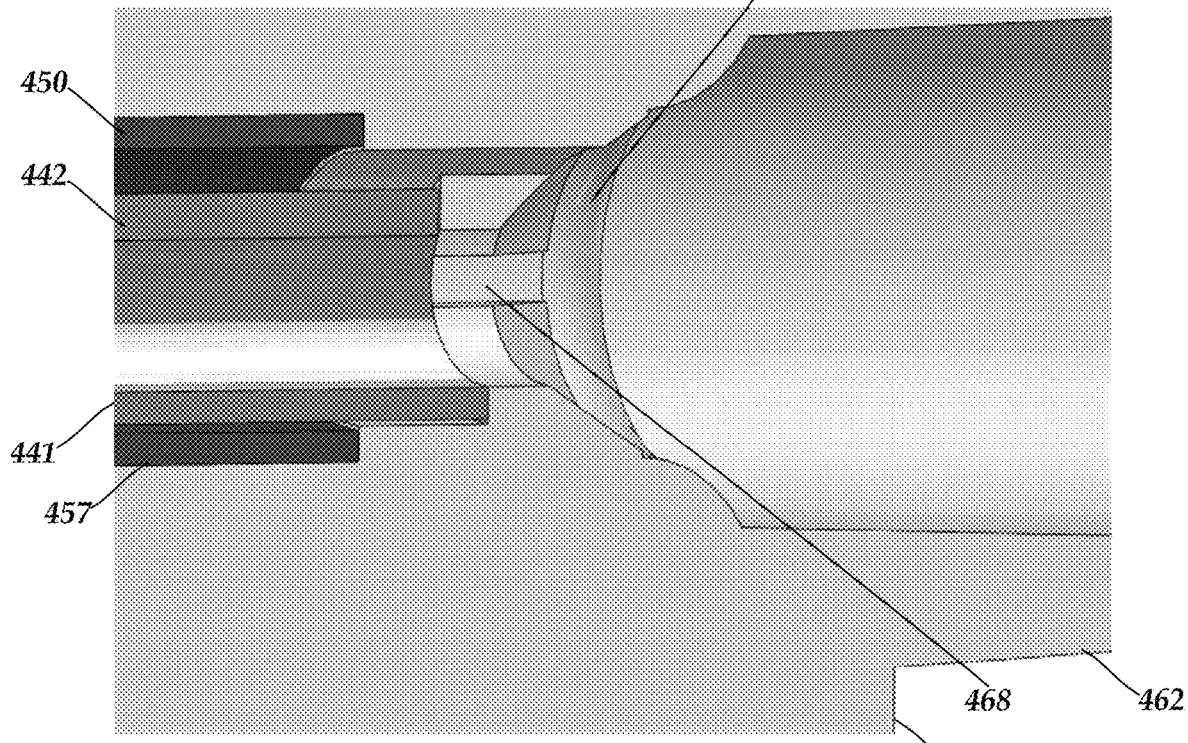
FIG. 4F is a close-up schematic view of a portion of the view of FIG. 4E with the proximal end portions of the needle and splittable sheath attached to the hub.

FIG. 4E is a cutaway view of a portion of the hub 460 illustrating features within the hub and FIG. 4F is an expanded portion of hub 460 illustrating the attachment of the proximal end 441 of the needle 442 and proximal end 457 of the splittable sheath 450 inside the hub. The needle 442 and splittable sheath 450 are attached to the hub 460 using any suitable method or material. Preferably, the attachment of the hub 460 to proximal end 441 of the needle 442 and proximal end 457 of the splittable sheath 450 should be sufficient so that the hub 460 remains attached to the proximal end 441 of the needle 442 and proximal end 457 of the splittable sheath 450 when the splittable sheath 450 and hub 460 are split and separated.

The hub 460 defines a hub lumen 459 that is in communication with the open channel 444 of the needle 442 and through which the needle stylet 470 and lead 103 can be inserted into the open channel of the needle. In at least some embodiments, the hub 460 defines a taper 467 of the hub lumen between the small-bore connector 451 and the region in which the proximal end 441 of the needle 442 is positioned to facilitate a smooth insertion of the needle stylet 470 and lead 103 into the open channel 444 of the needle 442.

In at least some embodiments, the hub 460 further defines a first shoulder 469a against which the proximal end 441 of the needle 442 is positioned and a second should 469b against which the proximal end 457 of the splittable sheath 450 is positioned. In at least some embodiments, the hub 460 further defines one or two gaps 468 in the first and second shoulders 469a, 469b to facilitate reliable splitting of the hub along the intended lines demarcated by the gaps and which may be further demarcated by corresponding slits or weakened regions 463a, 463b (FIG. 4D) on the exterior of the hub. FIG. 4G is a view into the hub lumen 459 from the proximal end of the hub 460 illustrating the small-bore connector 451, taper 467, and gaps 468, as well as the slits or weakened regions 463a, 463b in the small-bore connector. In at least some embodiments, the hub 460 further defines a notch 455 which receives a portion of the needle stylet 470, as described in more detail below, and which is aligned with the slot 446 of the needle 442.

Figure 5A:
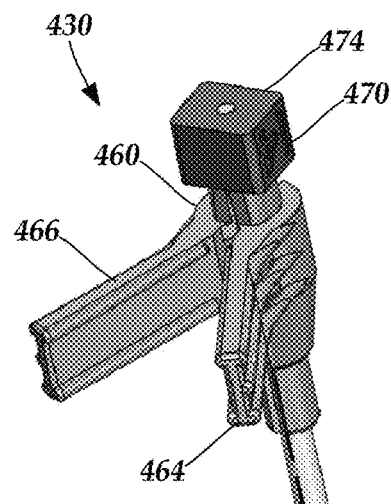
FIG. 5A is a schematic perspective view of one embodiment of the lead introducer of FIG. 3 including integrated needle/sheath and needle stylet.
Figure 5B:
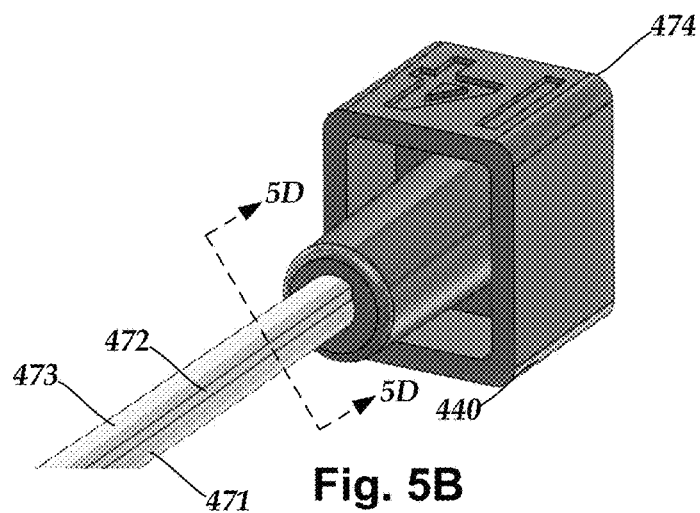
FIG. 5B is a schematic perspective close-up view of one embodiment of a proximal end portion of the needle style of FIG. 5A.
Figure 5C:
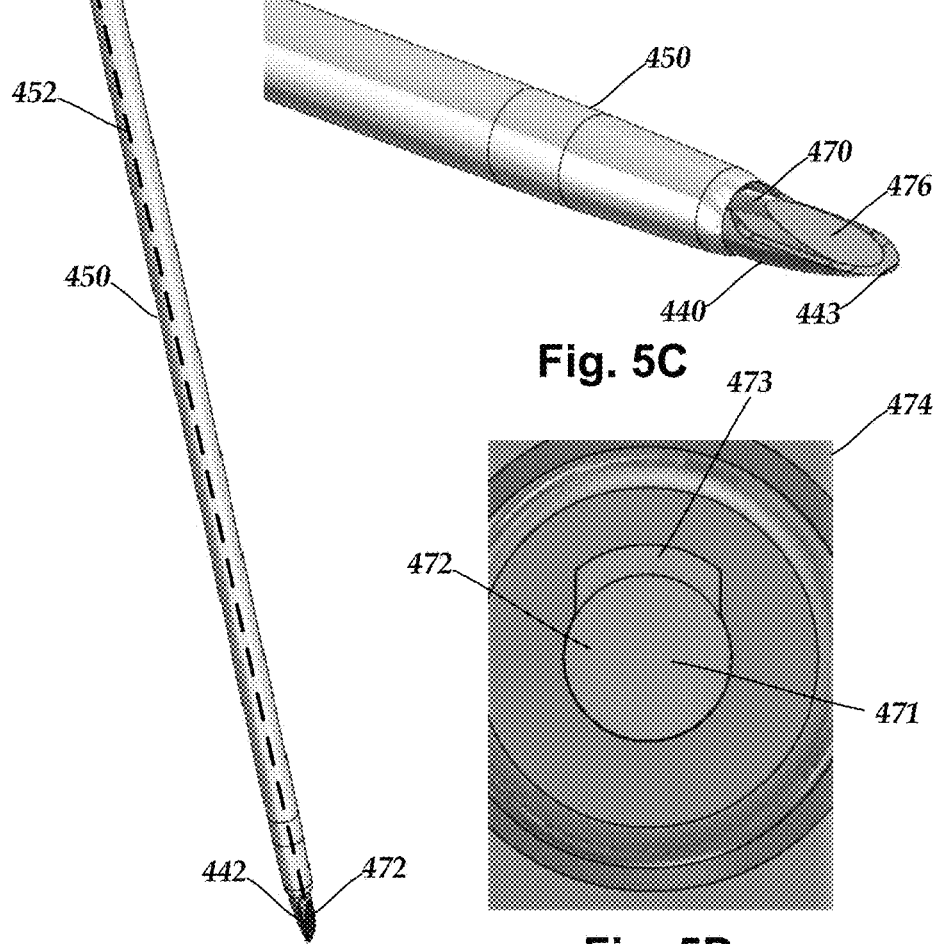
FIG. 5C is a schematic perspective close-up view of one embodiment of a distal end portion of the lead introducer of FIG. 5A.
Figure 5D:
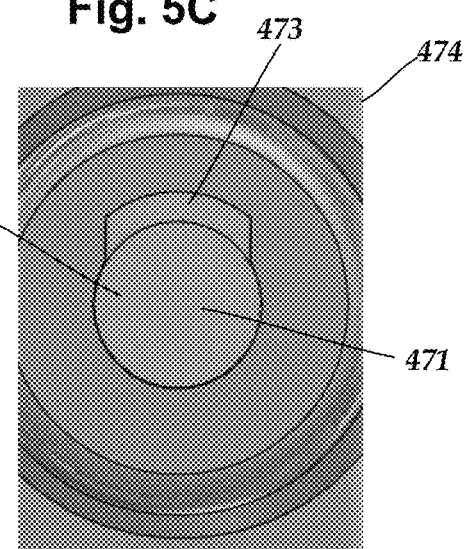
FIG. 5D is a schematic cross-sectional view of one embodiment of the needle stylet of FIGS. 5A and 5B.

FIG. 5A illustrates the lead introducer 430 with the needle stylet 470 inserted into the integrated needle/sheath 440. The needle stylet 470 may be inserted into the integrated needle/sheath 440 to improve stiffness and prevent or reduce tissue coring during insertion of the lead introducer 430 into the tissue of the patient. FIGS. 5B to 5D illustrate features of the needle stylet. The stylet body 470 is arranged to fit within the open channel 444 of the needle 442. FIG. 5B illustrates a stylet body 472 (which may also form a needle) and handle 474 of the needle stylet 470 where the handle is attached to the proximal end of the stylet body. In the illustrated embodiment, the handle 474 of the needle stylet is arranged to couple to the small-bore connector 451 of the hub 460.

FIG. 5C illustrates the distal end portion 476 of the stylet body 472 extending out of the splittable sheath 450 and disposed in the distal end of the needle 442. The distal end portion 476 of the stylet body 472 may have a slanted face with a sharpened end to facilitate insertion of the lead introducer into the tissue of the patient. In other embodiments, the distal end portion 476 of the stylet body 472 may have a Tuohy tip or blunt epidural tip.

In at least some embodiments, the needle stylet 470 is shaped such that the needle stylet 470 does not separate laterally from the open channel 444 when the needle stylet 470 is received by the needle 442. FIG. 5D is a partial cross-sectional view of a portion of the handle 474 and the stylet body 472 to illustrate that, at least in some embodiments, the stylet body 472 includes a cylindrical portion 471 and a stiffening portion 473 that extends from the cylindrical portion 471. In at least some embodiments, the stiffening portion 473 is sized and arranged to fit into the slot 446 (FIG. 4C) of the needle 442 when the needle stylet 470 is inserted into the integrated needle/sheath 440. The stiffening portion 473 may also be sized and arranged to fit into the notch 455 (FIG. 4G) in the hub 460. The stiffening portion 473 may run an entire length of the body 472 (or at least until the distal end portion 476) or may terminate at any point along the length of the body 472. In at least some embodiments, the stiffening portion 473 may terminate distal of the handle 474.

Figure 6A:
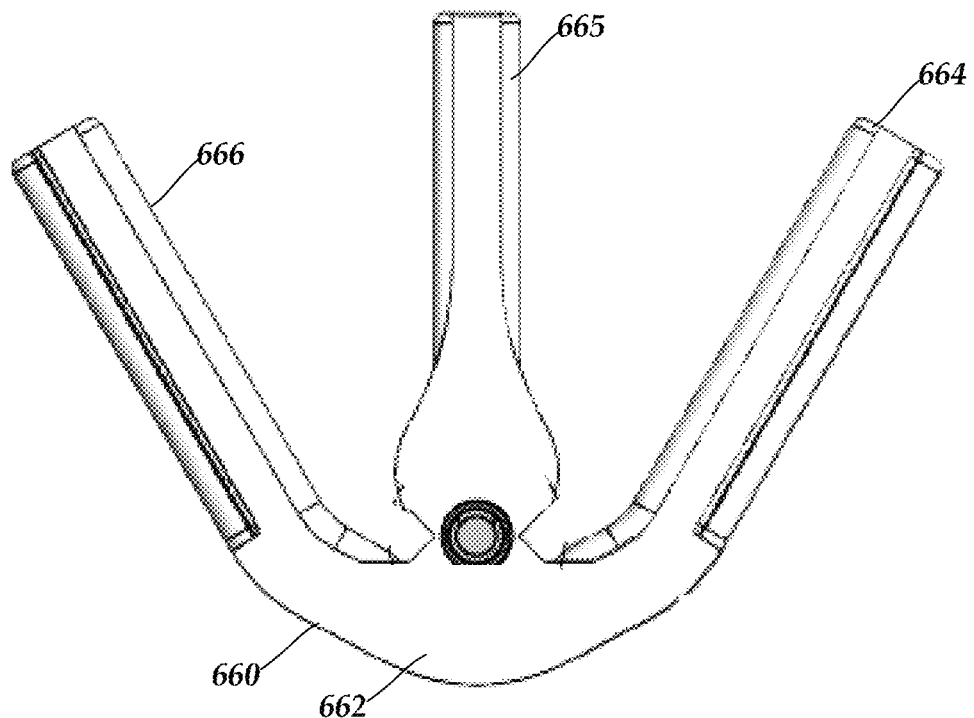
FIG. 6A is a schematic end view of an embodiment of an integrated needle/sheath with an arrangement of three pull-apart tabs.
Figure 6B:
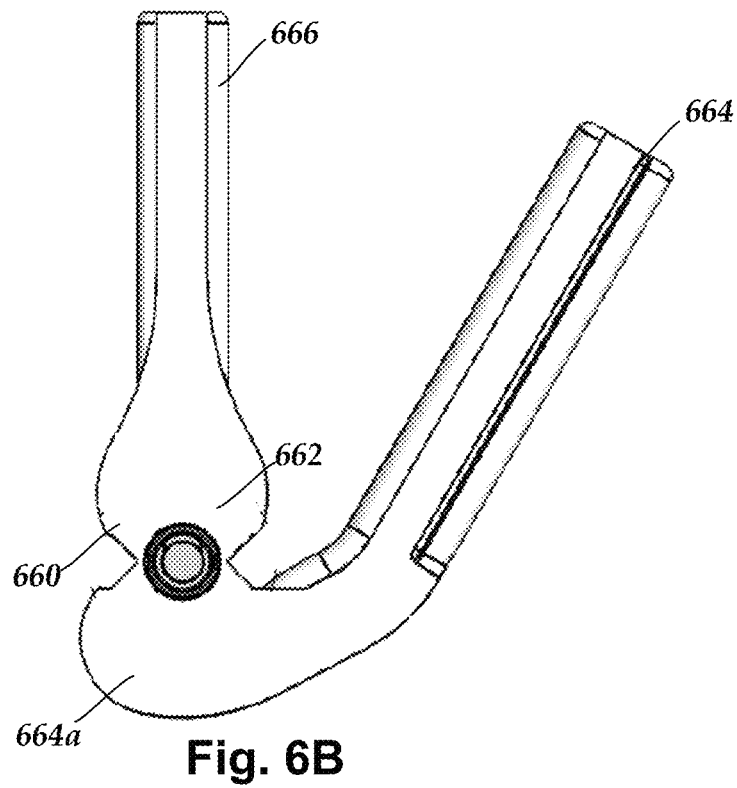
FIG. 6B is a schematic end view of another embodiment of an integrated needle/sheath with an arrangement of two pull-apart tabs.

FIGS. 6A and 6B illustrate two examples of different pull-apart tab arrangements for the lead introducer. It will be recognized that these are simply examples of pull-apart tab arrangements and that any other suitable arrangement of two or more pull-apart tabs can be used.

In FIG. 6A, the hub 660 of the lead introducer includes a body 662 and three pull-apart tabs 664, 665, 666. The three pull-apart tabs 664, 665, 666 can be arranged symmetrically with the two outer pull-apart tabs 664, 666 arranged equidistant from the center pull-apart tab 665. In other embodiments, the two outer pull-apart tabs 664, 666 can be arranged with different distances, or at different angles, from the center pull-apart tab 665.

In FIG. 6B, the hub 660 includes a body 662 and two pull-apart tabs 664, 666. One pull-apart tab 664 includes an extension 664a that wraps around a portion of the body 662 to form a more lever-like arrangement to facilitate application of torque when separating the hub 660 into two portions.

Figure 7:
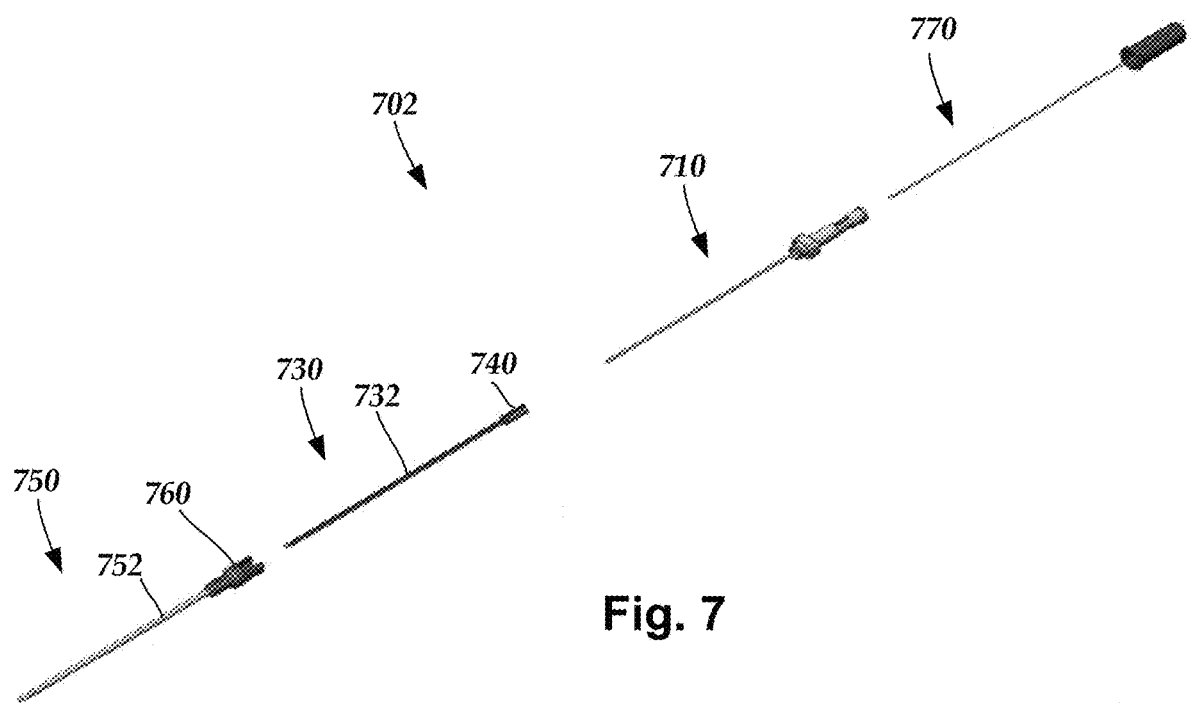
FIG. 7 is a schematic perspective exploded view of one embodiment of a lead introducer configured for facilitating implantation of a lead of an electrical stimulation system into a patient, the lead introducer including a multi-piece insertion needle, a splittable member, and an optional stylet.

FIG. 7 is a schematic perspective exploded view of another embodiment of a lead introducer 702 configured and arranged to facilitate implantation of an electrical stimulation system into a patient. The lead introducer 702 includes a multi-piece insertion needle 708, a splittable member 750, and a stylet 770. The multi-piece insertion needle 708 includes an inner needle 710 that is insertable into an outer needle 730. Additional examples of this lead introducer, as well as further details about embodiments of this lead introducer, are disclosed in U.S. Patent Application Publication Nos. 2011/0224680, 2014/0039586, 2014/0276927, 2015/0073431, 2015/0073432, and 2016/0317800, all of which are incorporated by reference in their entirety.

During implantation of the lead, the outer needle 730 is disposed within the splittable sheath 750. The outer needle includes a needle hub 740 and a body 732. The splittable sheath 750 includes a sheath body 752 and sheath hub 760.

Figure 8:
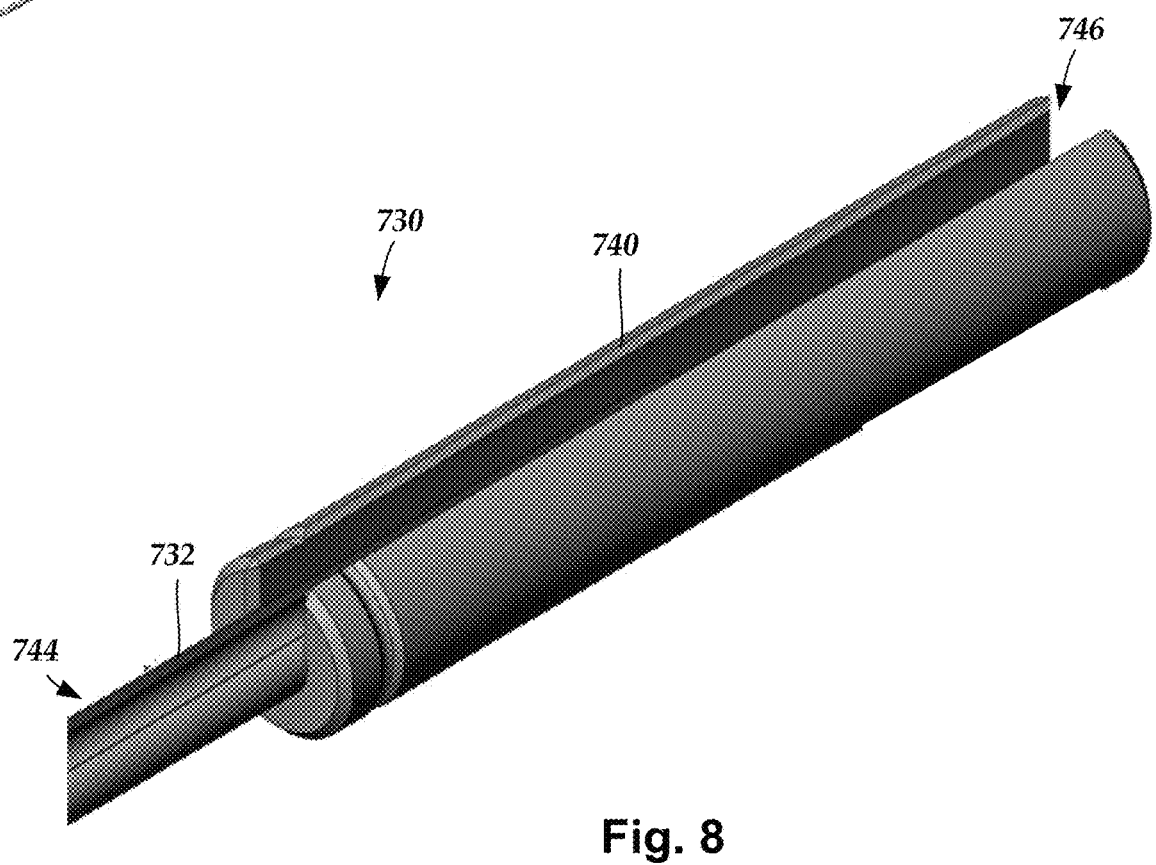
FIG. 8 is a schematic perspective view of one embodiment of a proximal end portion of an outer needle of the lead introducer of FIG. 7.

FIG. 8 illustrates a proximal portion of the outer needle 730 including the needle hub 740. The body 732 and needle hub 740 of outer needle 742 define an open channel 744 and a slot 746. When the outer needle 730 is disposed in the splittable sheath 750 and a lead 103 is inserted into the open channel 744 of the outer needle 730, the lead 103, as it is being pushed into the outer needle, may buckle so that a portion of the lead pops out of the slot 746 in the hub. When this happens, it may be difficult to continue to push the lead into the outer needle 730.

Figure 10B:
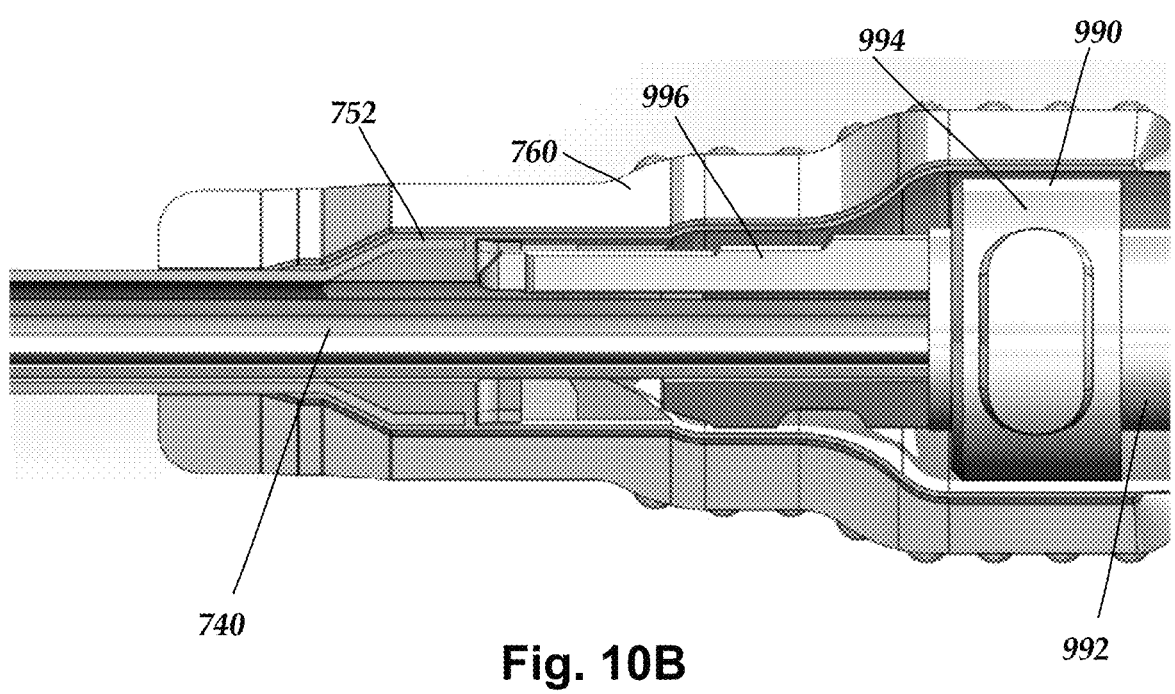
FIG. 10B is a schematic cross-sectional view of the lead guide of FIG. 9A, proximal end portion of the outer needle of FIG. 8, and hub of the splittable member of FIG. 7.

FIGS. 9A and 9B illustrate a lead guide 990 that can be inserted into the needle hub 740 of the outer needle 742, as illustrated in FIG. 10A, to prevent the lead 103 from popping out of the slot 746. The lead guide 990 includes a barrel 992, a stop ring 994, an extension 996 that extends distally from the stop ring and barrel, and a guide slot 998. The barrel 992 slides onto the needle hub 740, as illustrated in FIG. 10A, to cover the slot 746 of the needle hub. The lead guide 990 can be pushed into the sheath hub 760 and may be press fit into the sheath hub to prevent or reduce slippage. The stop ring 994 is provided to stop the lead guide 990 from sliding too far along the needle hub 740 and, at least in some embodiments, is stopped by the sheath hub 760, as illustrated in FIG. 10B. The extension 996 may also act as a stop against a portion 762 of the sheath hub 760 and may also orient the lead guide 990 relative to the needle hub 740 or sheath hub 760. After the lead 103 has been inserted fully into the outer needle 730, the lead guide 990 can be slid off the outer needle 703 and lead 103 with the lead passing through the guide slot 998.

Figure 11:
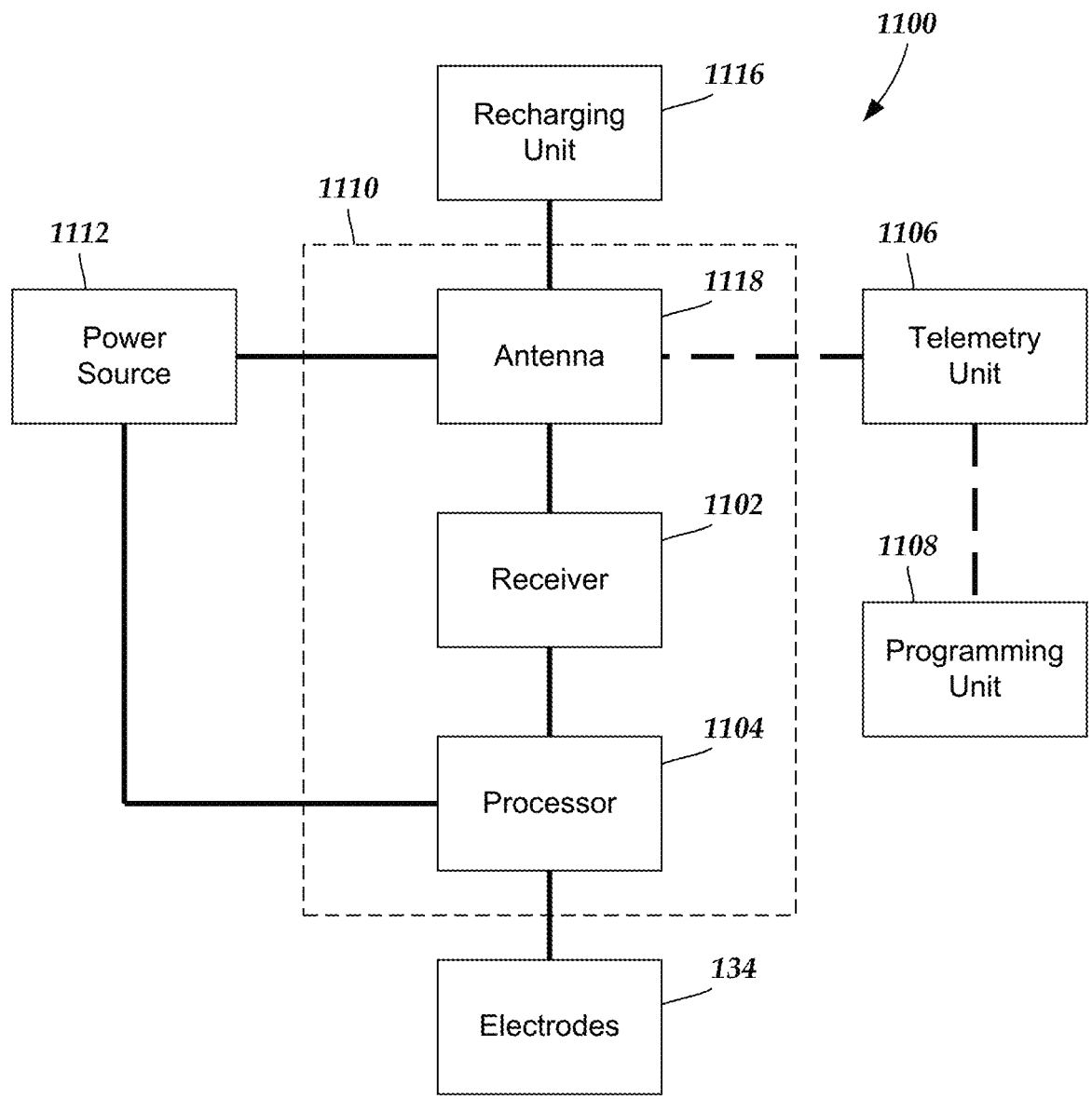
FIG. 11 is a schematic overview of one embodiment of components of a stimulation system, including an electronic subassembly disposed within a control module, according to the invention.

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, power source 1112, antenna 1118, receiver 1102, and processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 11,437,193, incorporated herein by reference in its entirety.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the lead body to stimulate nerve fibers, muscle fibers, or other body tissues near the electrical stimulation system. A processor 1104 is generally included to control the timing and electrical characteristics of the electrical stimulation system. For example, the processor 1104 can, if desired, control one or more of the timing, frequency, amplitude, width, and waveform of the pulses. In addition, the processor 1104 can select which electrodes can be used to provide stimulation, if desired. In some embodiments, the processor 1104 may select which electrode(s) are cathodes and which electrode(s) are anodes. In some embodiments, the processor 1104 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the electrical stimulation system. For example, the signals may be used to modify the pulses of the electrical stimulation system such as modifying one or more of pulse width, pulse frequency, pulse waveform, and pulse amplitude. The signals may also direct the electrical stimulation system 1100 to cease operation, to start operation, to start charging the battery, or to stop charging the battery. In other embodiments, the stimulation system does not include an antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected is:

1. A lead introducer comprising:
    an integrated sheath/needle comprising
        a splittable sheath having a length and a proximal end region and configured to split along the length of the splittable sheath into a first portion and a second portion, the splittable sheath defining a sheath lumen,
        a needle having a length and a proximal end region, the needle defining an open channel extending along the length of the needle, wherein the needle extends through the sheath lumen of the splittable sheath, and
        a hub coupled to the proximal end regions of the splittable sheath and the needle and configured to split into a first portion and a second portion, the hub defining a port and a hub lumen extending from the port and in communication with the open channel, wherein the needle is permanently attached to the first portion of the hub so that when the hub and splittable sheath are split into the respective first and second portions, the needle remains attached to the first portion of the hub.

2. The lead introducer of claim 1, wherein the hub comprises a body and at least two tabs extending from the body, wherein the hub is configured to split, along with the splittable sheath, using the at least two tabs.

3. The lead introducer of claim 2, wherein the hub comprises a small-bore connector coupled to the body and forming a portion of the port and hub lumen.

4. The lead introducer of claim 1, wherein the needle defines a slot along the length of the needle and configured for lateral release of a lead from the open channel of the needle.

5. The lead introducer of claim 4, wherein the lead introducer is configured so that splitting the hub into the first and second portions exposed the slot along the length of the needle to allow lateral release of the lead from the open channel of the needle.

6. The lead introducer of claim 1, further comprising a needle stylet configured for insertion into the open channel of the needle.

7. The lead introducer of claim 6, wherein the needle stylet comprises a stylet body and a handle coupled to the stylet body.

8. The lead introducer of claim 6, wherein the needle of the integrated sheath/needle comprises a body having a length, wherein the body defines two opposing ends that are separated from each other along the length of the body to define a slot.

9. The lead introducer of claim 8, wherein the stylet body comprises a cylindrical portion and a stiffening portion extending along at least a portion of the cylindrical portion, wherein the stiffening portion is configured to fit in the slot of the needle of the integrated sheath/needle.

10. The lead introducer of claim 1, wherein the needle is permanently attached to the first portion of the splittable sheath so that when the splittable sheath is split into the first and second portions, the needle remains attached to the first portion of the splittable sheath.

11. The lead introducer of claim 10, further comprising adhesive permanently attaching the needle to the first portion of the splittable sheath.

12. The lead introducer of claim 10, wherein the first portion of the splittable sheath is heat shrunk on the needle to permanently attach the needle to the first portion of the splittable sheath.

13. The lead introducer of claim 10, wherein the first portion of the splittable sheath is melted onto the needle to permanently attach the needle to the first portion of the splittable sheath.

14. The lead introducer of claim 1, wherein the first portion of the splittable sheath is permanently attached to the first portion of the hub so that when the hub is split into the first and second portions, the first portion of the splittable sheath remains attached to the first portion of the hub.

15. The lead introducer of claim 14, wherein the second portion of the splittable sheath is permanently attached to the second portion of the hub so that when the hub is split into the first and second portions, the second portion of the splittable sheath remains attached to the second portion of the hub.

16. An insertion kit comprising:

the lead introducer of claim 1; and a stimulation lead configured for implantation into a patient, the stimulation lead comprising a lead body having a distal end portion and a proximal end portion, a plurality of electrodes disposed at the distal end portion of the lead body, a plurality of terminals disposed at the proximal end portion of the lead body, and a plurality of conductive wires coupling the electrodes electrically to the terminals;

wherein the stimulation lead is insertable through the port of the hub of the lead introducer and into the hub lumen of the hub and the open channel of the needle.

17. An electrical stimulation system comprising:

the insertion kit of claim 16;

a control module configured to electrically couple to the stimulation lead of the insertion kit, the control module comprising a housing, and an electronic subassembly disposed in the housing; and a connector for receiving the stimulation lead, the connector comprising a connector housing defining a port for receiving the proximal end portion of the lead body, and a plurality of connector contacts disposed in the connector housing, the connector contacts configured to couple to the terminals of the stimulation lead when the proximal end portion of the stimulation lead is received by the connector housing.

18. The lead introducer of claim 1, wherein further comprising adhesive permanently attaching the needle to the hub.

19. The lead introducer of claim 1, wherein a portion of the hub is overmolded onto the needle to permanently attach the needle to the hub.

20. The lead introducer of claim 1, wherein the hub defines a first shoulder against which a proximal end of the needle is positioned and a second shoulder against which a proximal end of the splittable sheath is positioned.

* * * * *